(12) United States Patent
Xu et al.

(10) Patent No.: US 10,238,590 B2
(45) Date of Patent: Mar. 26, 2019

(54) LIQUID ACTIVATION SYSTEM

(71) Applicant: COLGATE-PALMOLIVE COMPANY, New York, NY (US)

(72) Inventors: Guofeng Xu, Plainsboro, NJ (US); Steven Miller, Skillman, NJ (US); Jennifer Gronlund, Flemington, NJ (US)

(73) Assignee: Colgate-Palmolive Company, New York, NY (US)

( * ) Notice: Subject to any disclaimer, the term of this patent is extended or adjusted under 35 U.S.C. 154(b) by 155 days.

(21) Appl. No.: 14/365,088

(22) PCT Filed: Dec. 19, 2012

(86) PCT No.: PCT/US2012/070572
§ 371 (c)(1),
(2) Date: Jun. 12, 2014

(87) PCT Pub. No.: WO2013/096425
PCT Pub. Date: Jun. 27, 2013

(65) Prior Publication Data
US 2015/0086487 A1  Mar. 26, 2015

Related U.S. Application Data

(60) Provisional application No. 61/577,555, filed on Dec. 19, 2011.

(51) Int. Cl.
| *A61K 8/22* | (2006.01) |
| *A61K 8/362* | (2006.01) |
| *A61Q 11/00* | (2006.01) |
| *A61K 8/36* | (2006.01) |
| *A61K 8/73* | (2006.01) |
| *A61K 8/81* | (2006.01) |
| *A61K 8/88* | (2006.01) |
| *A61K 8/02* | (2006.01) |
| *A61K 8/49* | (2006.01) |
| *A61Q 19/10* | (2006.01) |

(52) U.S. Cl.
CPC ............ *A61K 8/362* (2013.01); *A61K 8/0283* (2013.01); *A61K 8/36* (2013.01); *A61K 8/49* (2013.01); *A61K 8/731* (2013.01); *A61K 8/8152* (2013.01); *A61K 8/88* (2013.01); *A61Q 11/00* (2013.01); *A61Q 19/10* (2013.01); *A61K 2800/52* (2013.01)

(58) Field of Classification Search
CPC ............. A61K 9/08; A61K 8/02; A61K 8/362
See application file for complete search history.

(56) References Cited

U.S. PATENT DOCUMENTS

| 3,535,421 A | 10/1970 | Briner et al. |
| 3,678,154 A | 7/1972 | Widder et al. |
| 4,041,149 A * | 8/1977 | Gaffar ............... A61K 8/24 424/57 |
| 4,885,155 A | 12/1989 | Parran, Jr. et al. |
| 4,905,825 A | 3/1990 | Brader |
| 5,302,373 A | 4/1994 | Giacin et al. |
| 5,776,435 A | 7/1998 | Gaffar et al. |
| 2002/0077264 A1 * | 6/2002 | Roberts ............ B65D 75/38 510/296 |
| 2002/0086039 A1 * | 7/2002 | Lee ................... A61K 8/22 424/401 |
| 2004/0062723 A1 | 4/2004 | Zaidel et al. |
| 2006/0024246 A1 * | 2/2006 | Maitra ............ A61K 8/0208 424/49 |
| 2006/0058206 A1 | 3/2006 | Walls et al. |
| 2006/0198803 A1 * | 9/2006 | Giniger ............. A61K 8/046 424/70.4 |
| 2006/0229226 A1 * | 10/2006 | Giniger ............. A61K 8/046 510/392 |

FOREIGN PATENT DOCUMENTS

| CN | 1268885 | 10/2000 | |
| CN | 1646675 | 7/2005 | |
| CN | 1960696 | 5/2007 | |
| CN | 1960701 | 5/2007 | |
| CN | 101925346 | 12/2010 | |
| EP | 2609830 | 3/2013 | |
| WO | WO 02/089759 | 11/2002 | |
| WO | WO2005094766 | 10/2005 | |
| WO | WO2005094768 | 10/2005 | |
| WO | WO 2005094768 A1 * | 10/2005 | ............... A61K 8/22 |
| WO | WO 07/111630 | 10/2007 | |
| WO | WO2008041045 | 4/2008 | |

OTHER PUBLICATIONS

Kuzmenko et al., 2002. Beginnings of Chemistry. Modern Course for entering universities. in 2 values, v.1.—M: Examine, 384 p.; pp. 174-178.
Tzanov et al., 2002, "Hydrogen peroxide generation with immobilized glucose oxidase for textile bleaching," Journal of Biotechnology 93:87-94.
International Search Report and the Written Opinion issued in International Application PCT/US2012/70522 dated Feb. 11, 2014. WO.
Mintel, "Mouthwash," Database accession No. 1201644; Oct. 2009.
Stay, "Test Tube Science:Fizzle Fizzle," The Nature of the Chemical Blog, retrieved from the Internet http://natureofthechemicalblog.blogspot.com.au/2011/04/test-tube-schience-fizzle-fizzle.html.

* cited by examiner

*Primary Examiner* — Micah Paul Young

(57) ABSTRACT

Described herein are compositions comprising an unactivated liquid, an immobilized sparingly soluble acid or base, such that during storage the unactivated liquid is not in contact with the immobilized sparingly soluble acid or base, but upon use, the unactivated liquid contacts the immobilized sparingly soluble acid or base, whereby the pH of the liquid is altered, thereby activating the liquid to provide a benefit; together with variant and alternative designs, methods of making and using the compositions, and components thereof.

19 Claims, No Drawings

LIQUID ACTIVATION SYSTEM

CROSS-REFERENCE TO RELATED PATENT APPLICATIONS

The present application is a U.S. national stage entry under 35 U.S.C. § 371 of Patent Cooperation Treaty Patent Application No. PCT/US12/70572, filed Dec. 19, 2012, which claims priority to U.S. Provisional Patent Application No. 61/577,555, filed Dec. 19, 2011, the entirety of which is incorporated herein by reference.

BACKGROUND

Arginine and other basic amino acids have been proposed for use in oral care and are believed to have significant benefits in combating cavity formation and tooth sensitivity. Combining these basic amino acids with minerals having oral care benefits, e.g., fluoride and calcium, to form a mouthwash presents challenges. For example, the basic amino acid tends to raise the pH, but at higher pH, the mineral ions such as fluoride and calcium tend to form salts and to be less available for delivery to the teeth. Moreover, the higher pH has the potential to cause irritation in the mouth. At neutral pH or acidic pH, however, a system utilizing arginine bicarbonate (which the art teaches is preferred and which is found in marketed arginine-based oral care products) may release carbon dioxide, leading to bloating and bursting of the containers upon storage. Other formulation excipients, such as betaine (trimethyl glycine) have oral care benefits in some applications, but like arginine, tend to raise the pH of the formulation.

Another issue with mouthwash formulations is the difficulty of making formulations comprising enzymes, as the enzymes may be pH sensitive and may react with the formulation excipients.

Formulations comprising bleaching agents present further difficulties, as bleaching agents may be more stable at higher pH but more effective at lower pH.

Thus, there is frequently a problem that the optimum pH for formulation stability of a particular mouthwash formulation is quite different from the optimum pH for delivery of beneficial agents from the mouthwash. There is a need for a stable mouthwash product that provides a stable formulation, yet also provides efficient delivery of beneficial agents such as fluoride, calcium, and basic amino acids, and pH-sensitive agents like enzymes and bleaches.

SUMMARY

To address these problems, we have developed a system wherein the mouthwash formulation has a higher pH or lower pH in the bottle, then during dispensing of the formulation for use, the pH is lowered or raised by contact with a sparingly soluble acid or base, respectively, thereby to a level which enhances delivery of beneficial agents in the mouthwash. The change in pH can also provide aesthetic benefits, for example color change, effervescence, or flavor and fragrance release.

This concept, moreover, is not limited to mouthwash, but is also applicable to personal care products, such as liquid soaps, and home care products, such as surface cleansers.

The invention therefore provides, in one embodiment, a pH activation system comprising an unactivated liquid in a container, the container containing in a separate part, an immobilized sparingly soluble acid or base, such that during storage the unactivated liquid is not in contact with the immobilized sparingly soluble acid or base, but upon use, the unactivated liquid contacts the immobilized sparingly soluble acid or base, whereby the pH of the liquid is altered, thereby activating the liquid, e.g., wherein the pH alteration activates the liquid by providing one or more of enhanced availability of mineral ions, e.g., fluoride in a mouthwash, enhanced deposition of a complex comprising a basic amino acid and a mineral ion in a mouthwash, enhanced activity of an enzyme or enhanced reactivity of an enzyme substrate, enhanced activity of a bleaching agent, more acceptable pH for use on skin or in mouth, color change, effervescence, flavor change, or fragrance change.

In another embodiment, the invention provides a method of activating a liquid, e.g., a mouthwash, personal care product or home care product, comprising contacting the liquid with an immobilized sparingly soluble acid or base to alter the pH of the liquid just prior to use, e.g., thereby activating the liquid as described in the foregoing paragraph; and methods of tooth whitening or cleaning or of treating conditions of the oral cavity such as gingivitis, dental plaque or halitosis, or reducing demineralization of the enamel, comprising applying a mouthwash thus activated to the oral cavity; and methods of cleaning surfaces comprising applying a liquid surface cleanser thus activated to a surface; and methods of cleaning the skin, comprising a liquid skin care product thus activated to the skin.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The invention provides, e.g., a liquid product (Product 1), e.g., a mouthwash product, skin care product or home care product, comprising a container having a first compartment containing immobilized sparingly soluble acid or base, e.g., solid particles or matrix comprising sparingly soluble acid or base and a second compartment, one or more additional compartments each containing a unactivated liquid, optionally different unactivated liquids where there are more than one additional compartments, and a connection to the first compartment so as to permit flow of the unactivated formulation(s) into the first compartment upon use, and the first compartment having an aperture for dispensing the mouthwash formulation(s) following contact with the immobilized sparingly soluble acid or base, such that during storage the unactivated liquid is not in contact with the immobilized sparingly soluble acid or base, but upon use, the unactivated liquid contacts the immobilized sparingly soluble acid or base, whereby the pH of the liquid is altered, e.g., wherein the pH alteration activates the liquid by providing one or more of enhanced availability of mineral ions, e.g., fluoride, enhanced deposition on the teeth of a complex comprising a basic amino acid and a mineral ion, enhanced activity of an enzyme or enhanced reactivity of an enzyme substrate, enhanced activity of a bleaching agent, more acceptable pH for use on skin or in mouth, color change, effervescence, flavor change, or fragrance change.

For example, the invention provides
  1.1. Product 1 wherein the connection to the first compartment comprises a one way valve, e.g., a flap valve or a ball valve, permitting the liquid to flow into the first compartment, but restricting flow back into the one or more additional compartments.
  1.2. Product 1 or 1.1 comprising a pump which pumps the liquid(s) into the first compartment and out the aperture.
  1.3. Product 1 or 1.1 wherein the activated liquid is dispensed by pouring the liquid(s) from the one or more additional compartments through the first compartment and out the aperture.
  1.4. The product according to any of the foregoing claims wherein the connection to the first compartment is sealed when not in use, e.g., by a ring twist closure.
  1.5. The product according to any of the foregoing claims wherein the unactivated liquid(s) is an orally acceptable mouthwash formulation.
  1.6. The product according to any of the foregoing claims wherein the unactivated liquid(s) is an orally acceptable mouthwash formulation comprising an effective amount of fluoride, e.g. wherein the sparingly soluble
  1.7. The product according to any of the foregoing claims wherein the unactivated liquid(s) is an orally acceptable mouthwash formulation comprising a basic amino acid, e.g., selected from arginine, lysine, citrullene, ornithine, creatine, histidine, diaminobutanoic acid, diaminoproprionic acid, salts thereof and/or combinations thereof, for example L-arginine in free or salt form, e.g. arginine bicarbonate.
  1.8. The product according to any of the foregoing claims wherein the unactivated liquid(s) is an orally acceptable mouthwash formulation comprising one or more calcium salts.
  1.9. The product according to any of the foregoing claims wherein the unactivated liquid(s) comprises a halochromic dye (i.e., a dye which changes color in response to changes in pH), e.g. selected from Resazurin, Gentian violet (Methyl violet 10B), Leucomalachite green, Thymol blue (first transition), Methyl yellow, Bromophenol blue, Congo red, Methyl orange, Bromocresol green, Methyl red, Azolitmin, Bromocresol purple, Bromothymol blue, Phenol red, Neutral red, Naphtholphthalein, Cresol Red, Phenolphthalein, Hydrangea flowers, Anthocyanins, and Litmus, e.g., selected from Phenolphthalein, Hydrangea flowers, Anthocyanins, and Litmus.
  1.10. The product according to any of the foregoing claims wherein the unactivated liquid(s) comprises a profragrance that converts to a fragrance upon pH change; for example an ester or ether compound that hydrolyzes rapidly to provide a fragrant alcohol when the pH changes, e.g., wherein the profragrance is (2-dimethoxy)ethyl-benzene, the pH of the unactivated liquid is alkaline, and the immobilized sparingly soluble acid or base is an acid, such that when the pH of the unactivated liquid is reduced upon use to neutral or acidic pH, the (2-dimethoxy)ethyl-benzene hydrolyzes to provide phenylethyl alcohol (rose fragrance).
  1.11. The product according to any of the foregoing claims wherein the unactivated liquid(s) comprises a flavor, fragrance, or other ingredient in a microparticle matrix, wherein the microparticle matrix comprises a polymer that disintegrates when the pH changes, e.g., wherein the unactivated liquid has an acidic pH, and the microparticle matrix comprises a polycarboxyl compound which deprotonates and disintegrates at higher pH, e.g., acrylate polymer or co-polymer, acryloyl chloride-lysine, hydroxypropyl methylcellulose acetate succinate, thereby releasing the flavor, fragrance, or other ingredient.
  1.12. The product according to any of the foregoing claims wherein the unactivated liquid comprises a salt selected from carbonates, bicarbonates, and combinations thereof, e.g., sodium bicarbonate or arginine bicarbonate, e.g., wherein the immobilized sparingly soluble acid or base is an acid, such that when the pH of the unactivated liquid is reduced upon use, carbon dioxide is released, causing effervescence.
  1.13. The product according to any of the foregoing claims wherein the unactivated liquid comprises an enzyme and an enzyme substrate and the pH of the unactivated liquid is outside the range where the enzyme is active on the substrate.
  1.14. The foregoing product wherein the enzyme is a glucose oxidase having an optimal pH range of less than 7, the substrate is glucose, and the immobilized sparingly soluble acid or base is an acid, such that when the pH of the unactivated liquid is reduced upon use, hydrogen peroxide is produced.
  1.15. The product according to any of the foregoing claims wherein the unactivated liquid comprises hydrogen peroxide, e.g., wherein the pH of the unactivated liquid is low, e.g., at a pH optimal for stability of hydrogen peroxide, e.g, less than pH 4, immobilized sparingly soluble acid or base is a base, such that the pH of the formulation is increased to a level less irritating to skin upon use.
  1.16. The product according to any of the foregoing claims wherein the immobilized sparingly soluble acid or base is an acid in solid form.
  1.17. The product according to any of the foregoing claims wherein the immobilized sparingly soluble acid or base is formic acid.
  1.18. The product according to any of the foregoing claims wherein the immobilized sparingly soluble acid or base is a base in solid form.
  1.19. The product according to any of the foregoing claims wherein the unactivated liquid comprises one or more agents selected from fluoride, antibacterial agents (e.g., triclosan or cetyl pyridinium chloride), arginine, betaine, potassium salt (e.g. potassium nitrate), flavorings, dyes, humectants, polymers and surfactants.
  1.20. The product according to any of the foregoing claims wherein the immobilized sparingly soluble acid or base comprises solid particles in an insoluble liquid permeable matrix.

In some embodiments, the sparingly soluble acid is an organic sparingly soluble acid. In other embodiments, the sparingly soluble acid is an acid phosphate salt. In some embodiments, the sparingly soluble acid is sodium acid pyrophosphate, sodium aluminum phosphate, monopotassium phosphate, or a mixture thereof. In some embodiments, the sparingly soluble acid is selected from: fumaric acid, propionic acid, pentanoic acid, and a combination of two or more thereof. In some embodiments, the sparingly soluble acid is fumaric acid.

In another embodiment, the invention provides a method of activating a liquid, e.g., a mouthwash, personal care product or home care product, comprising contacting the liquid with an immobilized sparingly soluble acid or base to alter the pH of the liquid just prior to use, e.g., thereby activating the liquid as described in the foregoing paragraph.

In another embodiment, the invention provides methods of tooth whitening or cleaning or of treating conditions of the oral cavity such as gingivitis, dental plaque or halitosis, or reducing demineralization of the enamel, comprising applying a mouthwash activated in accordance with the foregoing paragraph to the oral cavity, e.g., by rinsing the mouth with the activated mouthwash for a period of 15 seconds to one minute and then spitting the mouthwash out.

In another embodiment, the invention provides a method of cleaning surfaces comprising applying to a surface a liquid surface cleanser activated as described above.

In another embodiment, the invention provides methods of cleaning the skin comprising applying to the skin a liquid skin care product activated as described above.

In another embodiment, the invention provides a pH activation system for an oral care, personal care or home care product, comprising an unactivated liquid in a container, the container containing in a separate part, an immobilized sparingly soluble acid or base, such that during storage the unactivated liquid is not in contact with the immobilized sparingly soluble acid or base, but upon use, the unactivated liquid contacts the immobilized sparingly soluble acid or base, whereby the pH of the liquid is altered, thereby activating the liquid, e.g., wherein the pH alteration activates the liquid by providing one or more of enhanced availability of mineral ions, e.g., fluoride in a mouthwash, enhanced deposition of a complex comprising a basic amino acid and a mineral ion in a mouthwash, enhanced activity of an enzyme or enhanced reactivity of an enzyme substrate, enhanced activity of a bleaching agent, more acceptable pH for use on skin or in mouth, color change, effervescence, flavor change, or fragrance change.

Some embodiments of the present invention provide an oral care composition comprising a first component and a second component, the first component comprising an immobilized enzyme, and the second component comprising a flowable liquid comprising reactants, such that during storage the flowable liquid is not in contact with the immobilized enzyme, but upon use, the flowable liquid contacts the immobilized enzyme and the enzyme catalyzes a reaction involving the reactants in the flowable liquid to produce a whitening agent.

In some embodiments, the immobilized enzyme is adsorbed to an insoluble material, trapped in insoluble beads, covalently bonded to the insoluble material through a chemical reaction, attached by binding domain of the peptide having affinity for the insoluble material, or entrapped in an insoluble matrix.

In other embodiments, the enzyme comprises a polyhistidine tag, and the insoluble material comprises or is coated with metal, e.g. nickel or cobalt, to which the polyhistidine tag binds. In some embodiments, the insoluble material is a histidine-affinity media such as Ni Sepharose, NTA-agarose, His60 Ni, HisPur resin, or TALON resin. In some embodiments, the insoluble material is steel wool comprising nickel.

In some embodiments, the enzyme comprises a sequence binding to hydroxyapatite, and the insoluble material comprises hydroxyapatite. In some embodiments, the one or more enzymes comprises a perhydrolase. In some embodiments, the one or more enzymes comprise a perhydrolase and the flowable liquid comprises a peroxide source and a carboxy donor, e.g., a carboxylic acid or acyl compound, e.g., such that when the flowable liquid contacts the perhydrolase, the perhydrolase catalyzes a reaction between the peroxide and the carboxy donor to form a peracid.

In some embodiments, the flowable liquid comprises a carboxy donor selected from (i) one or more $C_{2-18}$ carboxylic acids, e.g $C_{2-6}$ carboxylic acids (e.g., acetic acid), including lower linear or branched alkyl carboxylic acids, optionally substituted with hydroxy and/or $C_{1-4}$ alkoxy; (ii) one or more hydrolysable and acceptable esters thereof (e.g. mono-, di-, and tri-glycerides and acylated saccarides) and (iii) mixtures thereof. In some embodiments, the flowable liquid comprises a carboxy donor selected from 1,2,3-triacetoxypropane (sometimes referred to herein as triacetin or glycerin triacetate) and acylated saccharides, e.g. acetylated saccharides.

In some embodiments, the flowable liquid comprises a carboxy donor which is reactive with a peroxide in the presence of a perhydrolase to provide a peracid, and which comprises an ester compound having solubility in water of at least 5 ppm at 25° C.

In some embodiments, the one or more enzymes comprise a perhydrolase and the flowable liquid comprises hydrogen peroxide and triacetin, e.g., such that when the flowable liquid contacts the perhydrolase, the perhydrolase catalyzes a reaction between the peroxide and the triacetin to produce peracetic acid. In some embodiments, the one or more enzymes comprise glucose oxidase and the flowable liquid comprises glucose, e.g., so that when the flowable liquid contacts the oxidase, the oxidase catalyzes the oxidation of glucose to hydrogen peroxide and D-glucono-δ-lactone.

In other embodiments, the one or more enzymes comprise a perhydrolase and a glucose oxidase, and the flowable liquid comprises glucose and triacetin, e.g., so that when the flowable liquid contacts the oxidase, the oxidase catalyzes the oxidation of glucose to hydrogen peroxide and D-glucono-δ-lactone, and the perhydrolase catalyzes a reaction between the peroxide and the triacetin to produce peracetic acid.

In some embodiments, the one or more enzymes comprise a perhydrolase and the flowable liquid comprises hydrogen peroxide, triacetin, and methylethyl ketone, e.g., such that when the flowable liquid contacts the perhydrolase, the perhydrolase catalyzes a reaction between the peroxide and the triacetin to produce peracetic acid, and the peracetic acid converts the ketone to the corresponding dioxirane.

In some embodiments, the flowable liquid comprises one or more agents selected from fluoride, antibacterial agents (e.g., triclosan or cetyl pyridinium chloride), arginine, betaine, a potassium salt (e.g. potassium nitrate), a flavoring, a dye, a humectant, a polymer and a surfactant. In other embodiments, the flowable liquid comprises a peroxide source and an acyl compound and optionally a ketone, in an orally acceptable carrier.

In some embodiments, the flowable liquid comprises hydrogen peroxide. In some embodiments, the flowable liquid comprises triacetin. In some embodiments, the flowable liquid further comprises fluoride.

In yet other embodiments, the flowable liquid further comprises an antibacterial agent, e.g., selected from triclosan (5-chloro-2-(2,4-dichlorophenoxyl)phenol); a zinc or stannous ion source; a quaternary ammonium compound such as cetylpyridinium chloride (CPC); a bisguanide such as chlorhexidine; and benzalkonium chloride, e.g., triclosan or cetylpyridinium chloride, e.g., in effective amounts, e.g., 0.001-1%, e.g., 0.01-0.5%.

In some embodiments, the flowable liquid further comprises a basic amino acid and/or ammonium acid compound, e.g., selected from arginine, in free or salt form and trimethyl glycine, and combinations thereof.

Some embodiments provide oral compositions wherein the flowable liquid further comprises flavorings, e.g., an essential plant oil, e.g. menthol. While other embodiments provide compositions wherein the flowable liquid further comprises a potassium salt, e.g, potassium citrate, potassium chloride, potassium tartrate, potassium bicarbonate, potassium oxalate, potassium nitrate; strontium salts, or mixtures thereof.

In some embodiments, the flowable liquid further comprises a humectant, e.g., selected from glycerin, propylene glycol, and sorbitol. In other embodiments, the flowable liquid further comprises a buffer, e.g., a phosphate buffer. In some embodiments, the flowable liquid further comprises one or more polymers.

In some embodiments, the flowable liquid further comprises one or more surfactants. In some embodiments, the flowable liquid further comprises an orally acceptable ketone, e.g., methyl ethyl ketone.

In other embodiments, the ingredients of the first and second component are present in amounts sufficient to provide, upon contact of the flowable liquid with the one or more enzymes, a whitening agent in an amount and concentration effective to whiten teeth.

Some embodiments provide a method of producing a whitening agent in a liquid oral care formulation, comprising contacting a liquid to an immobilized enzyme, wherein the enzyme reacts with one or more components in the liquid to provide the bleaching agent, and separating the resulting liquid comprising whitening agent from the enzyme. Other embodiments provide a method of whitening the teeth or treating gingivitis, dental plaque or halitosis, comprising preparing a liquid comprising a whitening agent in accordance with the embodiments described herein, and administering the liquid to the oral cavity, e.g., by rinsing the mouth with the liquid for a period of 15 seconds to one minute and then expectorating the liquid.

Orally Acceptable: All ingredients for use in the oral care, e.g., mouthwash, formulations described herein should be orally acceptable. By "orally acceptable" as the term is used herein is meant an ingredient which is present in the formulation as described in an amount and form which does not render the formulation unsafe, unpalatable or otherwise unsuitable for use in the oral cavity.

Topically Acceptable: All ingredients for use in the personal care formulations described herein, e.g. liquid soaps or cleansers, should be topically acceptable. By "topically acceptable" as the term is used herein is meant an ingredient which is present in the formulation as described in an amount and form which does not render the formulation unsafe or otherwise unsuitable for use on the skin.

Active Agents: The effective concentration of the active ingredients used herein will depend on the particular agent and the delivery system used. Actives, when present in compositions of the invention, are provided in effective amounts. Arginine, where present in a mouthwash, may be present at levels (expressed as weight of free base), of about 0.1 to about 3 wt %. Fluoride where present in a mouthwash may be present at levels of for example about 25 to about 250 ppm. Levels of antibacterial agents in a mouthwash will vary similarly, e.g., in some embodiments, antimicrobial agent is present at a concentration of from about 0.001 to about 1%, by weight, e.g. where the antimicrobial agent is cetylpyridinium chloride, e.g., at a concentration of about 0.05%, by weight, or where the antibacterial agent is triclosan, e.g. at a concentration of about 0.03% by weight.

Fluoride Ion Source: The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention thus may contain a source of fluoride ions or fluorine-providing ingredient in amounts sufficient to supply about 25 to about 250 ppm fluoride. Weights of fluoride salts to provide the appropriate level of fluoride ion will obviously vary based on the weight of the counter ion in the salt.

Oral or personal care products described herein may comprise humectants. Humectants useful herein include polyhydric alcohols such as glycerin, sorbitol, xylitol or low molecular weight PEGs, alkylene glycol such as polyethylene glycol or propylene glycol. In various embodiments humectants also function as sweeteners. In some embodiments, the humectant is present in the amount of about 1 to about 40% each by weight. In some embodiments, the humectant is sorbitol. In some embodiments sorbitol present at a concentration of from about 5 to about 25%, by weight. In some embodiments sorbitol present at a concentration of from about 5 to about 15%, by weight. In some embodiments, the sorbitol is present at a concentration of about 10%, by weight. Reference to sorbitol herein refers to the material typically as available commercially in 70% aqueous solutions. In some embodiments, the total humectant concentration is from about 1 to about 60%, by weight. In some embodiments, the humectant is glycerin. In some embodiments, glycerin is present at a concentration of from about 5 to about 15%, by weight. In some embodiments, glycerin present is at a concentration of about 7.5%, by weight. In some embodiments, the humectant is propylene glycol. In some embodiments, propylene glycol is present at a concentration of about 5 to about 15%, by weight. In some embodiments, propylene glycol is present at a concentration of about 7%, by weight.

The unactivated liquid in the foregoing embodiments may optionally comprise colorants. Colorants such as dyes may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sul-fophenyl-5-hydroxy-pyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-.DELTA.-3, 5-cycl-ohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. Typically, colorants if included are present in very small quantities.

The unactivated liquid in the foregoing oral care embodiments may optionally comprise flavorings. Flavor agents are known, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavor agents can be used individually or in admixture. Commonly used flavors include mints such as peppermint, artificial vanilla, cinnamon derivatives, and various fruit flavors, whether employed individually or in admixture. Generally, any flavoring or food additive, such as those described in Chemicals Used in Food Processing, publication 1274 by the National Academy of Sciences, pages 63-258, may be used. Typically, flavorants if included are present at 0.01-1%, by weight. In some embodiments, flavoring may be present in about 0.2%, by weight.

The unactivated liquid in the foregoing oral care embodiments may optionally comprise sweeteners. Sweeteners include both natural and artificial sweeteners. Suitable sweetener include water soluble sweetening agents such as monosaccharides, disaccharides and poysaccharides such as xylose, ribose, glucose (dextrose), mannose, galactose, fructose (levulose), sucrose (sugar), maltose, water soluble artificial sweeteners such as the soluble saccharin salts, i.e., sodium or calcium saccharin salts, cyclamate salts dipeptide based sweeteners, such a L-aspartic acid derived sweeteners, such as L-aspartyl-L-phenylalaine methyl ester (aspartame). In general, the effective amount of sweetener is utilized to provide the level of sweetness desired for a particular composition, will vary with the sweetener selected. This amount will normally be about 0.001% to about 5% by weight of the composition. In some embodiments, the sweetener is sodium saccharin and present at about 0.01% by weight of the composition.

The unactivated liquid in the foregoing oral care embodiments may optionally comprise breath freshening agents. Optional breath freshening agents may be provided. Any orally acceptable breath freshening agent can be used, including without limitation zinc salts such as zinc gluconate, zinc citrate and zinc chlorite, alpha-ionone and mixtures thereof. One or more breath freshening agents are optionally present in a breath freshening effective total amount.

The unactivated liquid in the foregoing oral care embodiments may include a tartar control (anticalculus) agent. Tartar control agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacyclo-heptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents include polycarboxylate polymers and polyvinyl methyl ether/maleic anhydride (PVME/MA) copolymers, such as those available under the Gantrez™ brand from ISP, Wayne, N.J.

In some embodiments, tartar control agent is present at a concentration of from about 0.01 to 10%, by weight. In some embodiments, the tartar control agent is present at a concentration of about 1%, by weight. In some embodiments, the tartar control agent also acts as a buffer. For example, in a phosphate buffer system, sodium phosphate monobasic is present at a concentration of from about 0.01 to about 5%, by weight and disodium phosphate is present at a concentration of from about 0.01 to about 5%, by weight, the precise ratio depending upon the other excipients in the formulation and the desired pH.

Other optional additives include antimicrobial (e.g., antibacterial) agents. Any orally acceptable antimicrobial agent can be used, including triclosan (5-chloro-2-(2,4-dichlorophenoxyl)phenol); zinc and stannous ion sources; quaternary ammonium compounds such as cetylpyridinium chloride (CPC); bisguanides such as chlorhexidine; and benzalkonium chloride. A further illustrative list of useful antibacterial agents is provided in U.S. Pat. No. 5,776,435 to Gaffar, et al. In some embodiments, antimicrobial agent is present at a concentration of from about 0.001 to about 1%, by weight. In some embodiments, the antimicrobial agent is cetylpyridinium chloride. In some embodiments, the cetylpyridinium chloride is present at a concentration of about 0.05%, by weight.

Antioxidants are another class of optional additives. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

Also optional, saliva stimulating agent, useful for example in amelioration of dry mouth may be included in the oral care embodiments. Any orally acceptable saliva stimulating agent can be used, including without limitation food acids such as citric, lactic, malic, succinic, ascorbic, adipic, fumaric, and tartaric acids, and mixtures thereof. One or more saliva stimulating agents are optionally present in a saliva stimulating effective total amount.

Optionally, an antiplaque (e.g., plaque disrupting) agent may be included in the oral care embodiments. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

Optional desensitizing agents in the oral care embodiments include potassium citrate, potassium chloride, potassium tartrate, potassium bicarbonate, potassium oxalate, potassium nitrate, strontium salts, and mixtures thereof. In some embodiments, a local or systemic analgesic such as aspirin, codeine, acetaminophen, sodium salicylate or triethanolamine salicylate can be used.

In some embodiments, the methods comprise the step of rinsing the oral cavity with a mouthwash composition as described above. In some embodiments, 5 ml or more of the composition is gargled. In some embodiments, 10 ml or more is used. In some embodiments, 10-50 ml is used. In some embodiments, 15-25 ml or more is used. In some embodiments, 15 ml or more is used. In some embodiments, the individual gargles with the composition multiple times per day. In some embodiments, the individual gargles with the composition on multiple days. In some embodiments, the individual gargles with the composition every 4 to 6 hours up to 6 times per day.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLE

Example 1

On Demand Mouthwash Delivery

Approximately 0.3 g of Fumaric Acid is added to a 3 ml syringe with a 25 mm filter tip (5 µm membrane). A solution of 10 µg/ml Resazurin in deionized water is prepared. The color of the solution is violet with an approximate pH of 7. 2 ml of violet Resazurin solution was added to the syringe, dispensed through the filter and collected. The dispensed solution is orange in color with an approximate pH of 2.3. An additional 2 ml of Resazurin solution was loaded and dispensed through the same syringe. This is repeated a third time with the same syringe. The entire experiment is repeated 3 times with 3 different Fumaric Acid loaded syringes. The results are summarized in the table below.

|  | Fumaric Acid (g) | Initial pH of Resazurin solution | Final pH of Dispensed Resazurin Solution | | |
| --- | --- | --- | --- | --- | --- |
|  |  |  | $1^{st}$ Dispense | $2^{nd}$ Dispense | $3^{rd}$ Dispense |
| Syringe 1 | 0.316 | 7.05 | 2.25 | 2.33 | 2.22 |
| Syringe 2 | 0.313 | 7.25 | 2.22 | 2.28 | 2.28 |
| Syringe 3 | 0.314 | 7.32 | 2.25 | 2.30 | 2.33 |

This experiment shows that the immobilized, sparingly soluble acid (here, fumaric acid) can repeatedly reduce the pH of the liquid, thereby activating the liquid to provide a color change with the halochromic dye (resazurin).

The invention claimed is:

1. An oral care mouthwash product comprising a container having:
   a first compartment containing solid particles or matrix which comprises sparingly soluble acid, wherein the sparingly soluble acid is immobilized within the first compartment and is selected from fumaric acid, propionic acid, pentanoic acid, or a combination thereof; and
   a second compartment containing an unactivated liquid, and
   a connection between the first compartment and the second compartment so as to permit flow of the unactivated liquid through the first compartment during use, and wherein the first compartment comprises an aperture for dispensing the mouthwash following passage through the first compartment while retaining the immobilized sparingly soluble acid solid particles or matrix;
   such that during storage the unactivated liquid is not in contact with the immobilized sparingly soluble acid and such that dispensing the liquid from the second compartment requires passing the liquid through the first compartment and out through the aperture, such that the unactivated liquid contacts the immobilized sparingly soluble acid, whereby the pH of the liquid is altered so as to activate the liquid; and
   wherein the unactivated liquid is an orally acceptable aqueous mouthwash formulation.

2. The product according to claim 1 wherein the pH alteration activates the liquid by providing one or more of the following benefits: enhanced availability of mineral ions, enhanced deposition on the teeth of a complex comprising a basic amino acid and a mineral ion, enhanced activity of an enzyme or enhanced reactivity of an enzyme substrate, enhanced activity of a bleaching agent, more acceptable pH for use in the mouth, color change, effervescence, flavor change, or fragrance change.

3. The product according to claim 1 wherein the unactivated liquid is an orally acceptable mouthwash formulation comprising an effective amount of fluoride.

4. The product according to claim 1 wherein the unactivated liquid is an orally acceptable mouthwash formulation comprising a basic amino acid.

5. The product according to claim 1 wherein the unactivated liquid is an orally acceptable mouthwash formulation comprising one or more calcium salts.

6. The product according to claim 1 wherein the unactivated liquid comprises a halochromic dye.

7. The product according to claim 1 wherein the unactivated liquid comprises a profragrance that converts to a fragrance upon pH change.

8. The product according to claim 1 wherein the unactivated liquid comprises a flavor, fragrance, or other ingredient in a microparticle matrix, wherein the microparticle matrix comprises a polymer that disintegrates when the pH changes, thereby releasing the flavor, fragrance, or other ingredient.

9. The product according to claim 1 wherein the unactivated liquid comprises a salt selected from carbonates, bicarbonates, and combinations thereof, such that when the pH of the unactivated liquid is reduced upon use, carbon dioxide is released, causing effervescence.

10. The product according to claim 1 wherein the unactivated liquid comprises an enzyme and an enzyme substrate and the pH of the unactivated liquid is outside the range where the enzyme is active on the substrate.

11. The product according to claim 10 wherein the enzyme is a glucose oxidase having an optimal pH range of less than 7, the substrate is glucose, such that when the pH of the unactivated liquid is reduced upon use, hydrogen peroxide is produced.

12. The product according to claim 1 wherein the immobilized sparingly soluble acid is in solid form.

13. The product according to claim 1 wherein the immobilized sparingly soluble acid is fumaric acid.

14. The product according to claim 1 wherein the unactivated liquid comprises one or more agents selected from fluoride, antibacterial agents, arginine, betaine, potassium salt, flavorings, dyes, humectants, polymers and surfactants.

15. The product according to claim 1 wherein the immobilized sparingly soluble acid comprises solid particles in an insoluble liquid permeable matrix.

16. A method of activating a liquid, wherein the liquid is a mouthwash, comprising contacting the liquid with an immobilized sparingly soluble acid selected from fumaric acid, propionic acid, pentanoic acid, or a combination thereof, which is immobilized to prevent dispensing and which alters the pH of the liquid just prior to use, thereby activating the liquid.

17. A method of tooth whitening or cleaning or of treating conditions of the oral cavity or reducing demineralization of the enamel, comprising applying a mouthwash activated in accordance with claim 16 to the oral cavity.

18. The product according to claim 4, wherein the basic amino acid is selected from arginine, lysine, citrullene, ornithine, creatine, histidine, diaminobutanoic acid, diaminoproprionic acid, and salts thereof and/or combinations thereof.

19. The product according to claim 6, wherein the dye is selected from Resazurin, Gentian violet (Methyl violet 10B), Leucomalachite green, Thymol blue (first transition), Methyl yellow, Bromophenol blue, Congo red, Methyl orange, Bromocresol green, Methyl red, Azolitmin, Bromocresol purple, Bromothymol blue, Phenol red, Neutral red, Naphtholphthalein, Cresol Red, Phenolphthalein, Hydrangea flowers, Anthocyanins, and Litmus.

* * * * *